United States Patent
Den Dulk et al.

(10) Patent No.: US 12,151,237 B2
(45) Date of Patent: Nov. 26, 2024

(54) AUTOMATED SYSTEM FOR PREPARING, DETECTING AND ANALYSING A FLUID SAMPLE

(71) Applicants: COMMISSARIAT A L'ENERGIE ATOMIQUE ET AUX ENERGIES ALTERNATIVES, Paris (FR); TOTALENERGIES ONETECH, Courbevoie (FR)

(72) Inventors: Remco Den Dulk, Grenoble (FR); Pierre Souquet, Pau (FR); Camille Echampard, Grenoble (FR); Raymond Charles, Grenoble (FR); Manuel Alessio, Grenoble (FR); Nicolas Sarrut-Rio, Grenoble (FR); Anne-Gaëlle Bourdat, Grenoble (FR); Mélissa Baque, Grenoble (FR); François Boizot, Grenoble (FR); Jean Malinge, Lescar (FR)

(73) Assignees: COMMISSARIAT A L'ENERGIE ATOMIQUE ET AUX ENERGIES ALTERNATIVES, Paris (FR); TOTALENERGIES ONETECH, Courbevoie (FR)

( * ) Notice: Subject to any disclaimer, the term of this patent is extended or adjusted under 35 U.S.C. 154(b) by 812 days.

(21) Appl. No.: 17/292,989

(22) PCT Filed: Nov. 7, 2019

(86) PCT No.: PCT/FR2019/052662
§ 371 (c)(1),
(2) Date: May 11, 2021

(87) PCT Pub. No.: WO2020/099763
PCT Pub. Date: May 22, 2020

(65) Prior Publication Data
US 2022/0001382 A1   Jan. 6, 2022

(30) Foreign Application Priority Data
Nov. 12, 2018   (FR) .................................... 18 60414

(51) Int. Cl.
| | | |
|---|---|---|
| *C12Q 1/6806* | (2018.01) | |
| *B01L 3/00* | (2006.01) | |
| *B01L 7/00* | (2006.01) | |
| *G01N 1/28* | (2006.01) | |
| *G01N 21/77* | (2006.01) | |
| *G01N 35/00* | (2006.01) | |
| *G01N 1/40* | (2006.01) | |

(52) U.S. Cl.
CPC ..... *B01L 3/502715* (2013.01); *B01L 3/50273* (2013.01); *B01L 7/52* (2013.01); *G01N 1/286* (2013.01); *G01N 21/77* (2013.01); *G01N 35/00069* (2013.01); *B01L 2200/10* (2013.01); *B01L 2300/0654* (2013.01); *B01L 2300/0681* (2013.01); *B01L 2300/0816* (2013.01); *B01L 2300/0864* (2013.01); *B01L 2400/0487* (2013.01); *G01N 2001/4088* (2013.01); *G01N 2021/7786* (2013.01); *G01N 2035/00237* (2013.01); *G01N 2035/00366* (2013.01)

(58) Field of Classification Search
CPC .................................................. C12Q 1/6806
See application file for complete search history.

(56) References Cited

U.S. PATENT DOCUMENTS

| | | |
|---|---|---|
| 2011/0014606 A1 | 1/2011 | Steinmetzer et al. |
| 2015/0197822 A1 | 7/2015 | Steinmetzer et al. |
| 2016/0168624 A1 | 6/2016 | Edwards et al. |
| 2017/0268041 A1* | 9/2017 | Gosselin ............... C12Q 1/686 |
| 2018/0099276 A1 | 4/2018 | Schmolke et al. |
| 2019/0153550 A1 | 5/2019 | Steinmetzer et al. |
| 2020/0102597 A1* | 4/2020 | Bourdat ............... G01N 1/4005 |

FOREIGN PATENT DOCUMENTS

WO   WO 2015/015175 A1   2/2015

OTHER PUBLICATIONS

N. Sandetskaya et al., An Integrated Lab-on-a-Chip Platform for the Isolation and Nucleic Acid-Based Detection of Pathogens, 3 Future Sci. OA 1-13 (2017).*

International Search Report issued on Jan. 15, 2020 in PCT/FR2019/052662 filed on Nov. 7, 2019, 3 pages.

Den Dulk, "FlowPad, a generic microfluidics platform for a wide range of applications", 11th EPIZONE Annual Meeting "Crossing Barriers" Sep. 19-21, 2017, Paris, France, Retrieved from the Internet: https://www.epizone-eu.net/upload_mim/0/c/6/37ale21a-2e43-42d4-ac53-6dcc6cf732el_2109%20KEYNOTE%20AM%20DEN%20DULK.pdf [retrieved on Jul. 24, 2019], pp. 1-30, XP055608282.

(Continued)

*Primary Examiner* — Randy Boyer
(74) *Attorney, Agent, or Firm* — Oblon, McClelland, Maier & Neustadt, L.L.P.

(57) ABSTRACT

An automated system for preparing, detecting and analyzing a first fluid sample containing biological species, the preparation, detection and analysis system including at least one fluidic cartridge that includes at least one fluidic concentration and lysis module and one fluidic detection module including an array of several amplification chambers arranged in parallel, an apparatus including a mechanical assembly comprising at least one movable rod fastened to the frame and comprising a free end arranged to cooperate with a flexible membrane of the fluidic concentration and lysis module, an optical measurement system for measuring fluorescence through one or more amplification chambers of the fluidic detection module of the cartridge, a control and processing unit.

9 Claims, 12 Drawing Sheets

(56) References Cited

OTHER PUBLICATIONS

Flaender et al., "Grinding Lysis (GL): a microfluidic device for sample enrichment and mechanical lysis in one", Sensors and Actuators B: Chemical, 2018, vol. 258, pp. 148-155, XP085338438.
Chen et al., "An integrated, self-contained microfluidic cassette for isolation, amplification, and detection of nucleic acids", Biomed Microdevices, 2010, vol. 12, No. 4, pp. 705-719, XP019814145.

* cited by examiner

AUTOMATED SYSTEM FOR PREPARING, DETECTING AND ANALYSING A FLUID SAMPLE

TECHNICAL FIELD OF THE INVENTION

The present invention relates to an automated preparation, detection and analysis system for a sample, which comprises a complete analysis device and a cartridge which is intended to be inserted in a removable manner in the analysis device. The preparation, detection and analysis system is particularly capable of detecting the presence of bacteria in a fluid sample.

PRIOR ART

The development of microorganisms, such as bacteria, fungi, algae, yeast, may have negative effects in an industrial installation. The development of biofilms may cause a number of incidents of damage including: corrosion, clogging, acidification, affecting the product.

It is therefore found to be necessary to carry out a monitoring of the presence of problematic microorganisms in an industrial environment by carrying out regular sampling in the sensitive zones. The sample may be removed in the form of a biofilm or in the form of a fluid, for example, production water originating from a petroleum reservoir.

The control and monitoring analyses of the microorganisms carried out on these fluids are often based on culture. Conventionally, the samples are inoculated with a range of dilutions in series, in a medium which contains nutrients and optimum physico-chemical conditions for the growth of the beneficial microorganisms and they are incubated at the ideal temperature. In the case of growth, the use of pH indicators or the formation of colored precipitates indicates the presence of microorganisms. This approach has the advantage of being simple, inexpensive and above all it can be used easily in a basic industrial installation control laboratory. However, it has a number of disadvantages:

- long response time as a result of the incubation time—this is because it may be from several days to several weeks if the doubling times are significant;
- some microorganisms cannot be cultivated under experimental conditions and will therefore not be detected;
- requirement for advanced training in order to learn the techniques of aseptic and/or anaerobic inoculations. Variations in results are thus possible from one operator to another;
- requirement for a degree of expertise in order to interpret the results obtained.

New molecular analysis methods based on DNA detection have been in development for some years. However, they require operators who are very well trained in the techniques of molecular biology, in particular with regard to pipetting and the use of micropipettes. The extraction of DNA is also quite a long step of the process, involving several steps of lysis, concentration and purification prior to analysis. Such analyses are therefore generally carried out outside the industrial site after preservation and transport of the samples to specialized laboratories.

Analysis solutions are described in the patent application US2011/014606A1 and in the publications set out below:

Remco Den Dulk: "*flowpad, a generic microfluidics platform for a wide range of applications*", 11th EPIZONE Annual meeting "Crossing Barriers" 19-21, September 2017, 21 Sep. 2017, XP055608282, Paris, France.

Flaender Mélanie et Al: "*Grinding lysis (GL): A microfluidic device for sample enrichment and mechanical lysis in one*", Sensors and Actuators: Chemical, Elsevier BV, NL, vol 258, 21 Nov. 2017, pages 148-155, XP085338438, ISSN: 0925-4005, DOI:10.1016/J.SNB.2017.11.082.

In order to be as close as possible to the ground and to enable a rapid reaction during proliferation, or precise optimization of the anti-bacterial processing operations used, there is therefore a need to have a preparation, detection and analysis system:

- which is completely automated in order to limit human interventions,
- which enables the nature and quantity of the biological species present in a sample, even a complex sample, to be determined in a reliable and rapid manner,
- which does not require the intervention of a qualified operator,
- which can be readily transported and can be deployed in a basic laboratory of an industrial site, and
- which can be adapted to the targets to be detected.

STATEMENT OF INVENTION

This object is achieved with an automated preparation, detection and analysis system for a first fluid sample containing biological species, said preparation, detection and analysis system comprising:

at least one fluid cartridge which comprises at least one fluid concentration and lysis module and a fluid detection module comprising a network of a plurality of amplification chambers which are arranged in parallel relative to a fluid distribution channel, said fluid lysis and concentration module comprising a concentration and lysis device which comprises a preparation chamber, an abrasive abutment surface which is produced in said preparation chamber, a filter and a flexible and deformable membrane which closes said chamber, a device comprising:
a frame which is provided with at least one plate which is intended to receive said fluid cartridge in a removable manner,
a mechanical assembly comprising at least one movable rod which is fixed to said frame and which comprises a free end which is arranged to cooperate with said flexible membrane of the fluid lysis and concentration module,
a pneumatic system controlled to enable circulation of a fluid through said cartridge,
at least one heating unit which is carried by the plate and which is arranged in order to heat the network of chambers in parallel during a cyclical or isothermal amplification reaction,
an optical system for measuring fluorescence through one or more of the amplification chambers of the fluid detection module of the cartridge,
a control and processing unit which is configured to implement an analysis sequence which comprises at least the following steps:
controlling the pneumatic system in order to inject the first fluid sample through the filter of the concentration and lysis device in order to recover the biological species present in the first sample,
controlling the pneumatic system in order to generate a flow of drying air in a fluid circuit of the fluid concentration and lysis module, said fluid circuit passing through said filter of the concentration and lysis device, controlling the mechanical assembly in order to activate the rod in an abutting movement of the flexible membrane against the abrasive abutment surface in order to lyse the biological species contained in the first fluid sample, controlling the pneumatic system in order to discharge a second fluid sample out of the preparation chamber to said fluid distribution channel of the cartridge, controlling the pneumatic system in order to fill in parallel and in a simultaneous manner the amplification chambers of the network with the second fluid sample, controlling the heating unit in order to heat said second fluid sample present in each chamber of the network, controlling the optical measurement system in order to measure the fluorescence in each amplification chamber containing a fraction of the second fluid sample, recording the fluorescene measurement results, applying an analysis algorithm to the measurement results obtained and generating qualitative and quantitative data of the biological species present in the first fluid sample.

According to a specific feature, the control and processing unit is configured to carry out:

a first module which is configured to send commands to the concentration and lysis device and to the pneumatic system, a second module which is configured to send commands to the heating unit, to the pneumatic system and to the optical measurement system, a third module which is configured to receive images from the optical measurement system and to process the images.

According to another specific feature, the system comprises a database which stores the previous analysis results and in that the third module is configured to refer to said database in order to generate concentration variation curves for each biological species detected.

According to another specific feature, each fluid module may comprise hydrophobic filters which are arranged on pneumatic channels which are connected directly to the pneumatic system.

According to another specific feature, the fluid concentration and lysis module and the fluid detection module comprises a plurality of fluid valves which can be controlled by the control and processing unit.

According to another specific feature, the system comprises a cartridge which integrates n fluid cartridges, with n being greater than or equal to 2.

According to another specific feature, the system comprises:

n mechanical assemblies which each comprise at least one rod which is associated with each cartridge, n heating units which are each arranged in order to heat the network of chambers of each cartridge, n/2 optical fluorescence measurement system which is configured to move between two positions in order to image the n cartridges of the system.

The invention also relates to a preparation, detection and analysis method for a fluid sample, implemented using the system as defined in one of the preceding claims, said method comprising the following steps:

controlling the pneumatic system in order to inject the first fluid sample through the filter of the concentration and lysis device in order to recover the biological species present in the first sample, controlling the pneumatic system in order to generate a flow of drying air in a fluid circuit of the fluid concentration and lysis module, said fluid circuit passing through said filter of the concentration and lysis device, controlling the mechanical assembly in order to activate the rod in a movement for abutting the flexible membrane against the abrasive abutment surface in order to lyse the biological species contained in the first fluid sample, controlling the pneumatic system in order to discharge a second fluid sample out of the preparation chamber to said fluid distribution channel of the cartridge, controlling the pneumatic system in order to fill in parallel and in a simultaneous manner the amplification chambers of the network with the second fluid sample, controlling the heating unit in order to heat said second fluid sample present in each chamber of the network, controlling the optical measurement system in order to measure the fluorescence in each amplification chamber containing a fraction of the second fluid sample, recording the fluorescence measurement results, applying an analysis algorithm to the measurement results obtained and generating qualitative and quantitative data of the biological species present in the first fluid sample.

The invention relates to use of the system as defined above in order to detect the presence of biological species in a fluid sample which is injected into said fluid cartridge of the system.

BRIEF DESCRIPTION OF THE FIGURES

Other features and advantages will be set out in the following detailed description given with reference to the appended drawings which are set out below and in which.

DETAILED DESCRIPTION OF AT LEAST ONE EMBODIMENT

The invention relates to an automated preparation, detection and analysis system for a fluid sample comprising biological species.

Biological species are intended to be understood, in a non-limiting manner, to be microorganisms, bacteria, cells, spores, fungi, etc.

The sample to be analyzed may be in the form of a fluid which is removed directly in situ or be obtained after dilution of a biofilm which is removed in situ. The term "fluid" is preferably intended to be understood to be a liquid.

Figure 1:
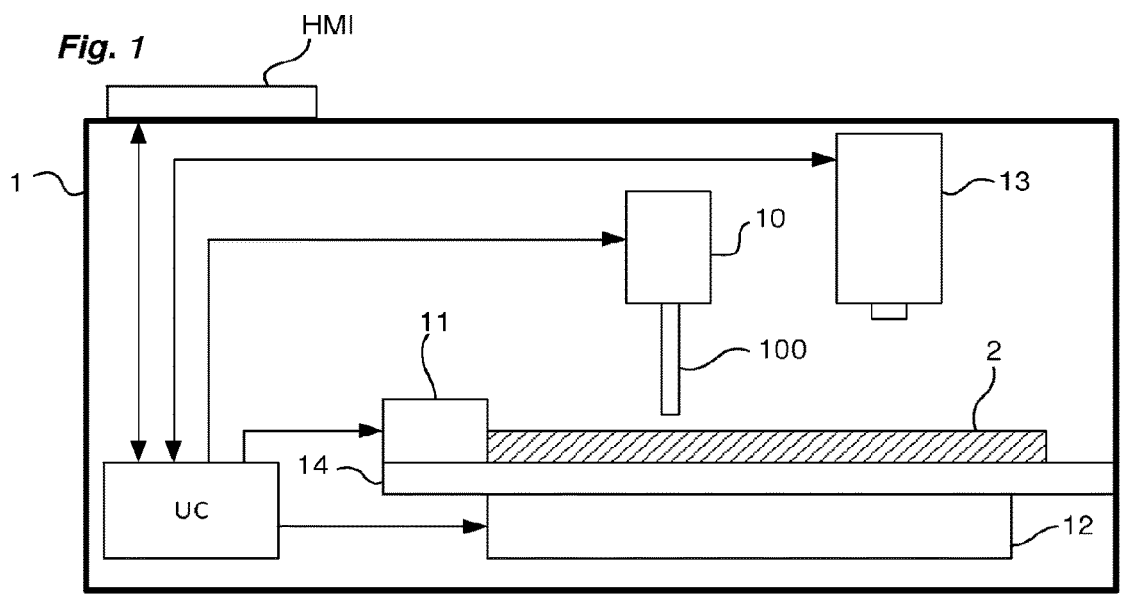
FIG. 1 is a schematic illustration of a preparation, detection and analysis system according to the invention.
Figure 2:
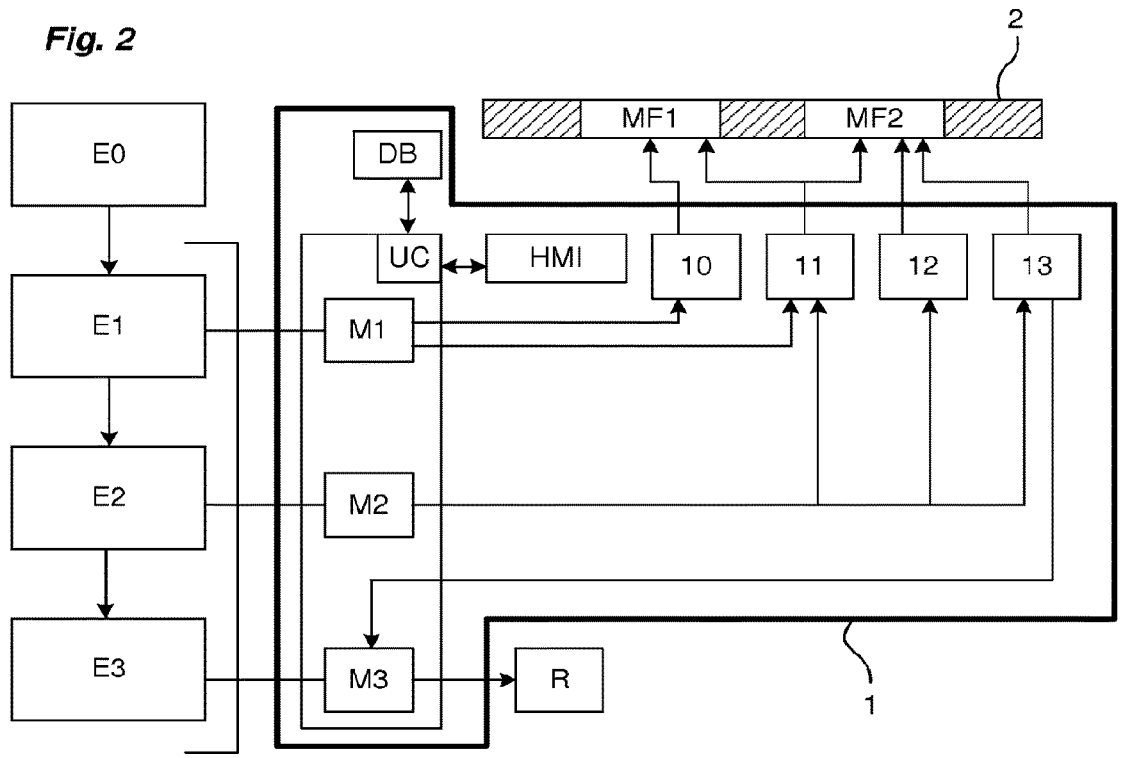
FIG. 2 is a diagram illustrating the operating principle of the preparation, detection and analysis system of the invention.

With reference to FIG. 2, an analysis of a liquid sample which may comprise biological species of the same type as those described above is conventionally carried out following the following different steps:
- a preliminary step E0 of preparing the sample taken. It will be seen that this step is not carried out by the preparation, detection and analysis system of the invention. It may, for example, involve diluting the sample if it is found to be solid. This is, for example, the case when the sample is a biofilm. Once prepared, the sample is in the form of a liquid with a volume equal to at least 1 ml.
- a second preparation step E1 which involves a concentration and a lysis. During this step, the sample prepared during the step E0 is first filtered in order to retain only the biological species. These biological species are then rinsed and purified with a suitable rinsing liquid. Then, the biological species are mechanically lysed in order to release a biological material to be analyzed. A new filtering can enable this biological material to be selected and it to be separated from the pollutants generated during lysis.
- a detection step E2, which can be implemented by using an amplification reaction of the Q-PCR type ("Quantitative-Polymerase Chain Reaction") or the type LAMP, RPA, NGS sequencing (Nanopore). The sample containing the biological material obtained after lysis can be mixed with dry reagents. The mixture is injected in liquid form into several amplification chambers which are arranged in parallel and which are supplied by a distribution channel. Each chamber may contain a different set of primers in accordance with the target to be detected. The chambers are heated in order to subject each sample present in a chamber to one or more successive thermal cycles of an amplification protocol or to maintain them at an isothermal temperature in the case of a detection of the LAMP or RPA type. Fluorescence images are captured during each thermal cycle of the amplification protocol and are recorded.
- a step E3 of analyzing the fluorescence images captured. An algorithm constructs the fluorescence intensity curve for each sample present in a chamber, taking into account the thermal cycles applied. The concentration of biological species targeted can thus be determined for each sample analyzed.

According to the invention, in order to implement the concentration and lysis step E1 and the detection step E2 and the analysis step E3, an automated preparation, detection and analysis system which comprises an analysis device 1 and at least one fluid cartridge 2 to be inserted into the analysis device 1 is used.

The system has the specific feature that specific functionalities are provided by the device 1 and that others are provided directly by the cartridge 2 which is inserted into the device. In other words, the analysis device and the cartridge must cooperate with each other in order to make the system work and the analysis cannot be carried out without one or other of these two entities.

The cartridge 2 is produced in the form of at least one fluidic card (even a microfluidic one). This card may have the format of a credit card or another format. It may be produced from a transparent material of the PMMA type (polymethyl methacrylate) or the like. The cartridge 2 inserted in the device advantageously has a configuration (in particular a fluidic configuration) which is always identical in order to cooperate with the elements of the device which are required to carry out the analysis.

The cartridge advantageously comprises two different fluid modules:
- a first fluid module MF1 which is intended for the concentration and lysis of the biological species present in the sample to be analyzed;
- a second fluid module MF2 which is dedicated to the detection of the biological species which are separated by the first module.

Figure 3:
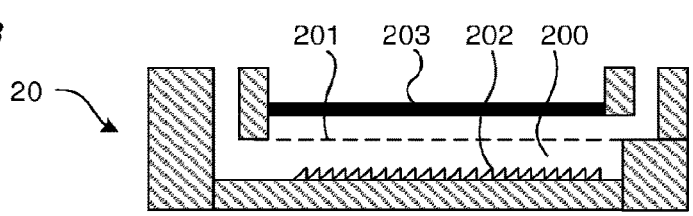
FIG. 3 schematically illustrates a concentration and lysis device which can be used in the preparation, detection and analysis system according to the invention.
Figure 4A:
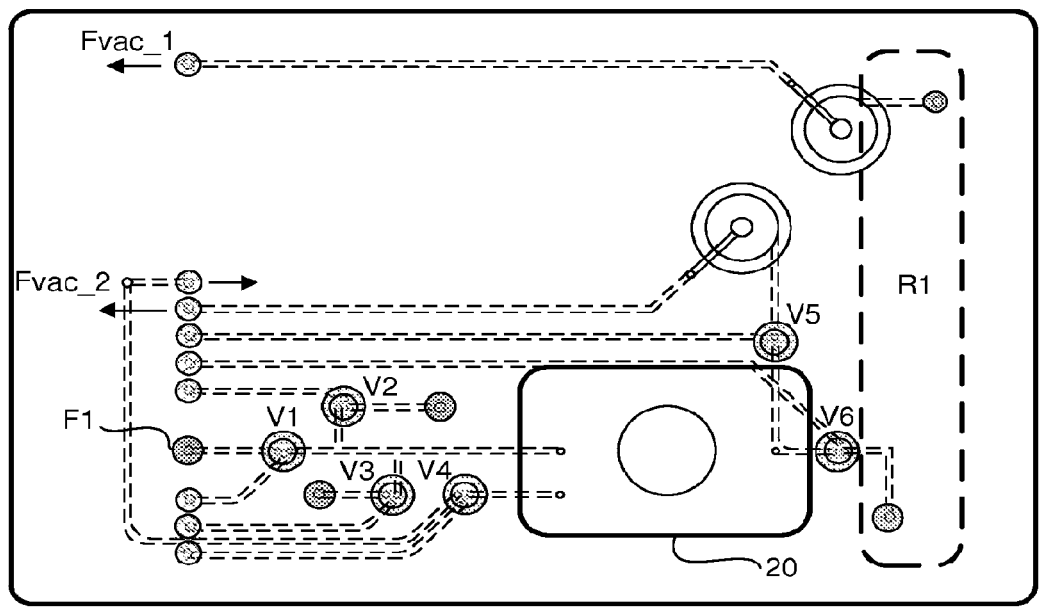
FIGS. 4A to 4M show the different steps implemented in the fluid concentration and lysis module used in the system of the invention.
Figure 4B:
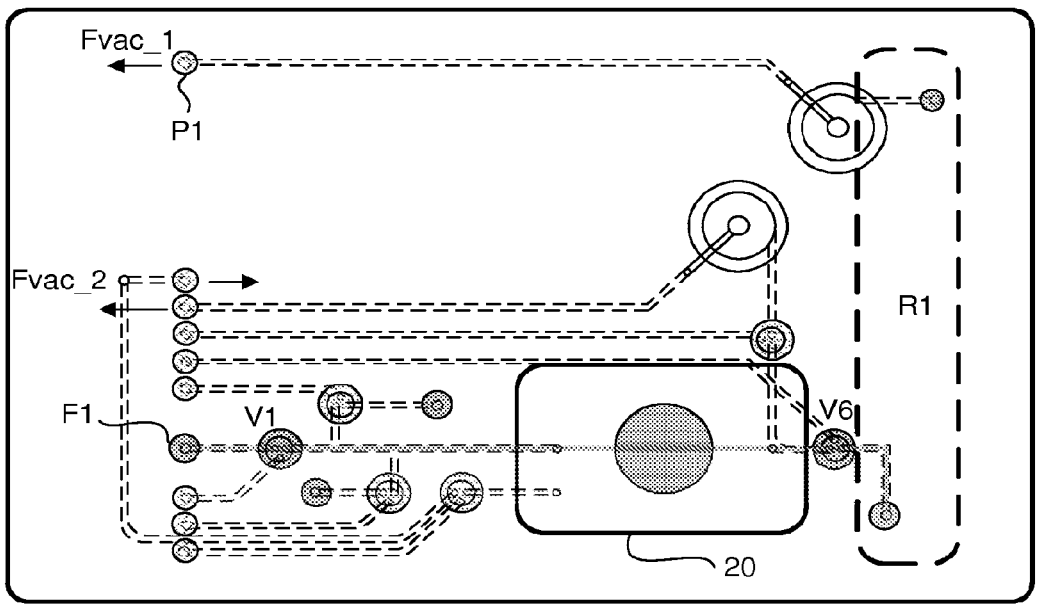
Figure 4C:
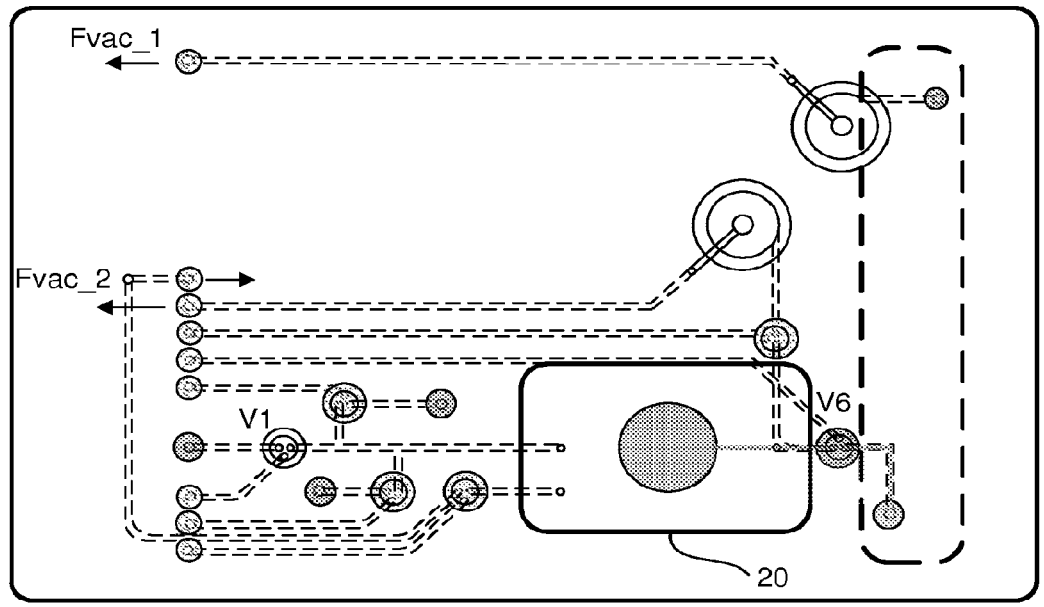
Figure 4D:
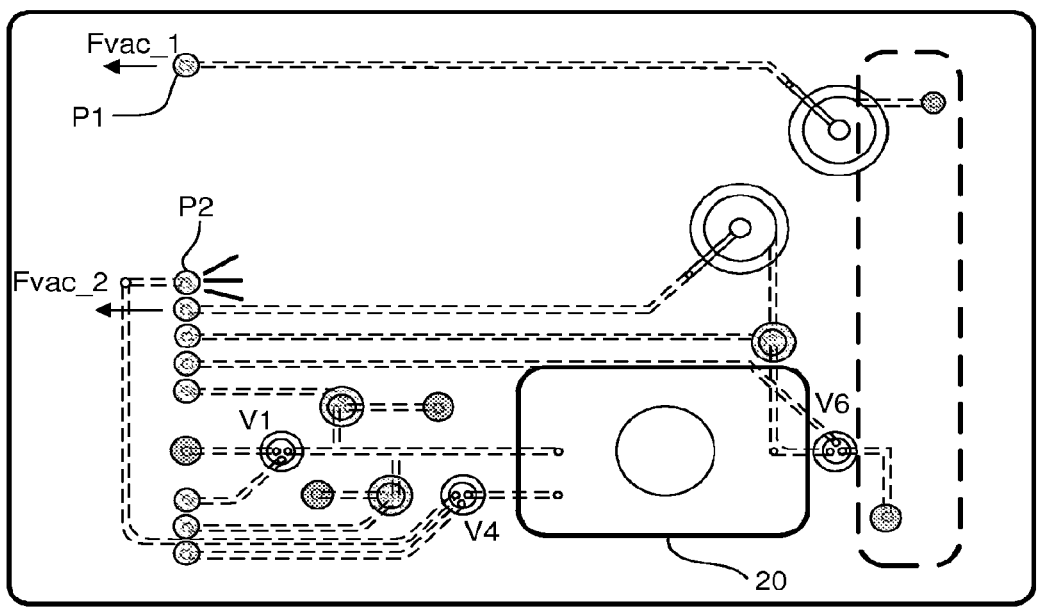
Figure 4E:
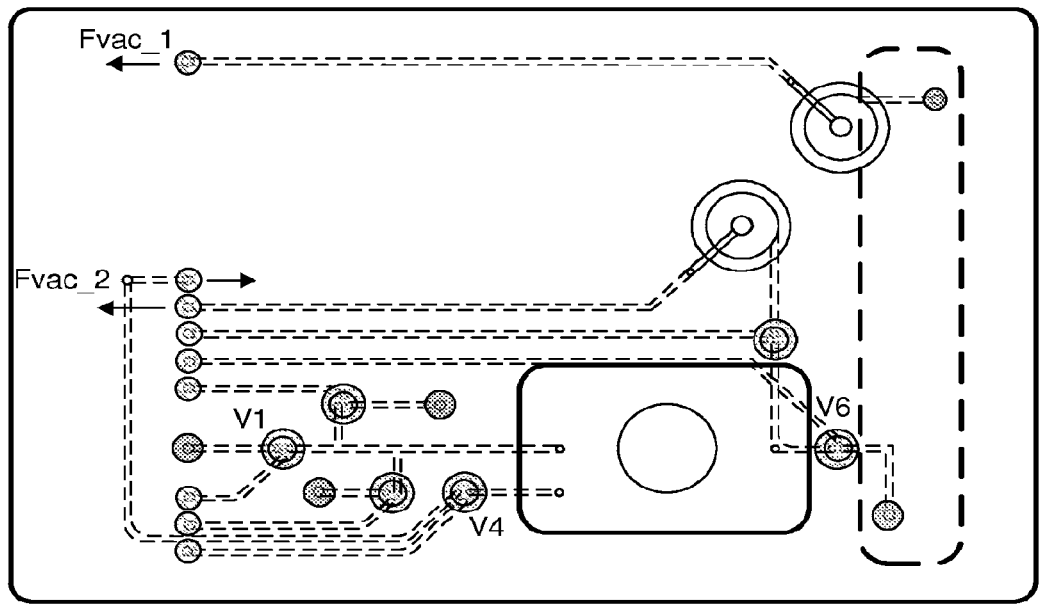
Figure 4F:
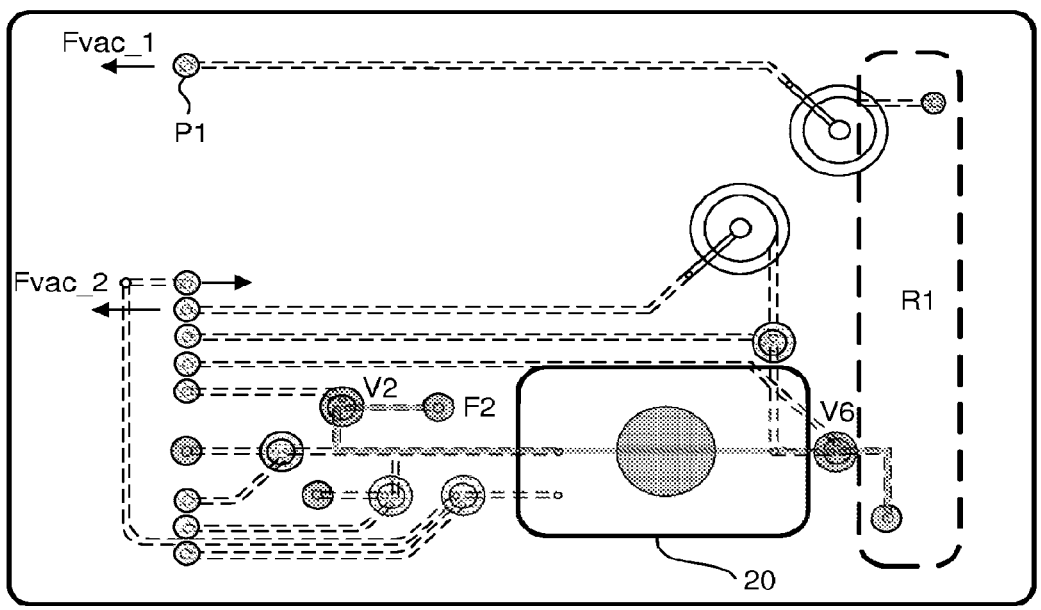
Figure 4G:
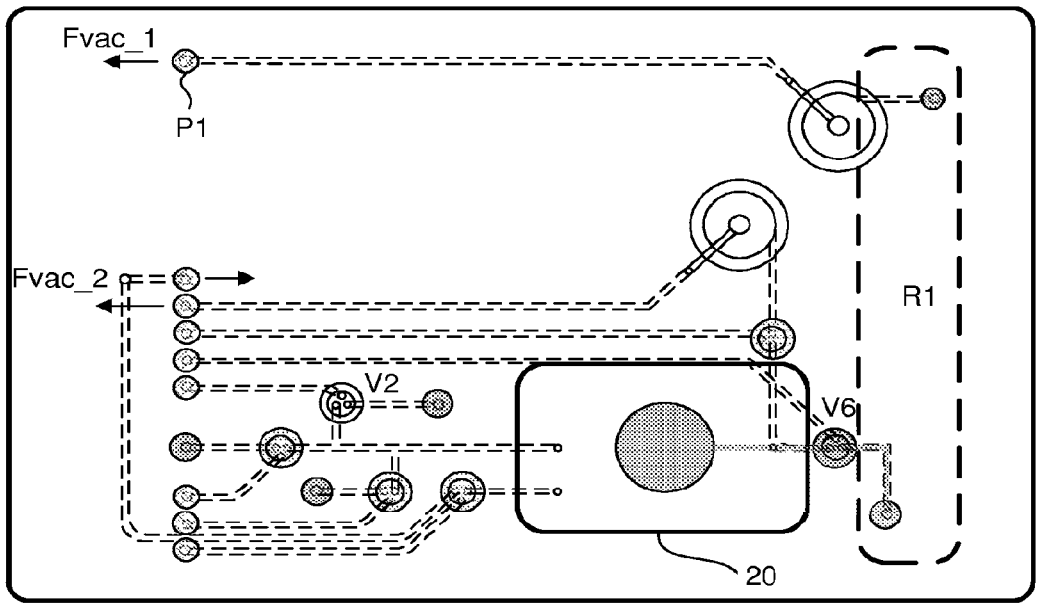
Figure 4H:
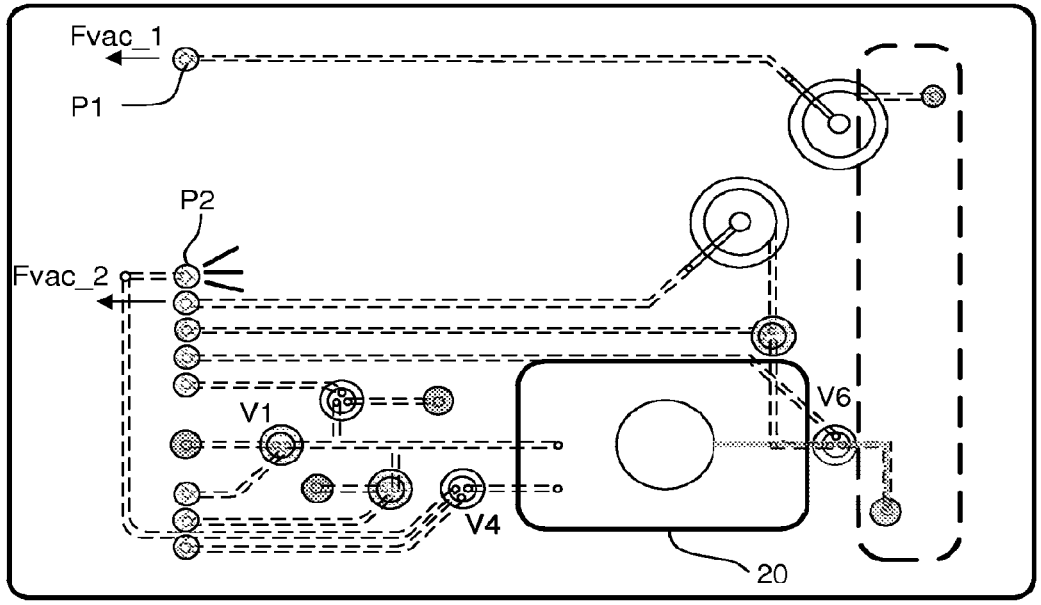
Figure 4I:
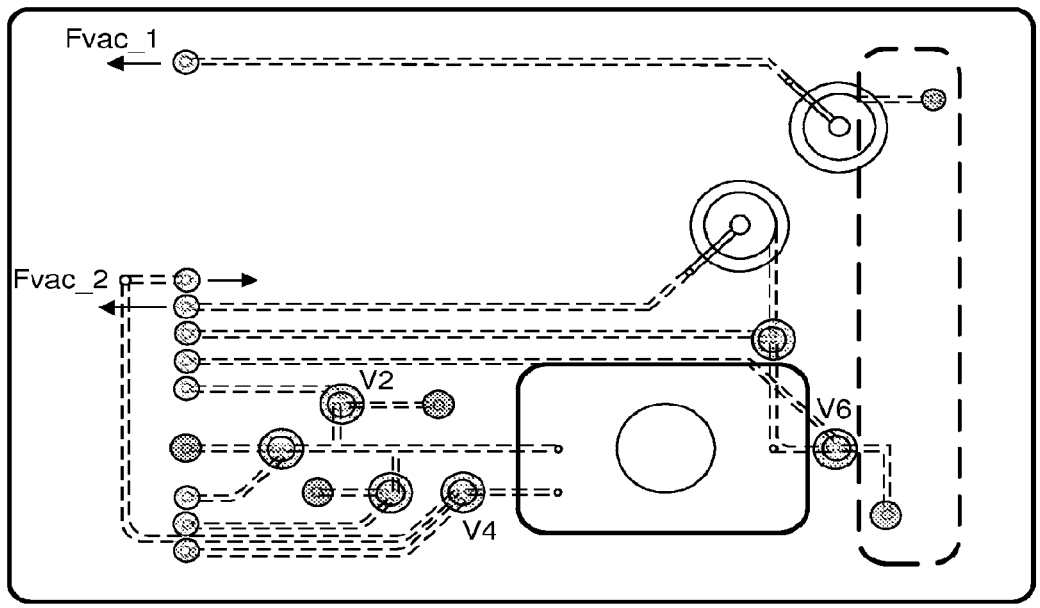
Figure 4J:
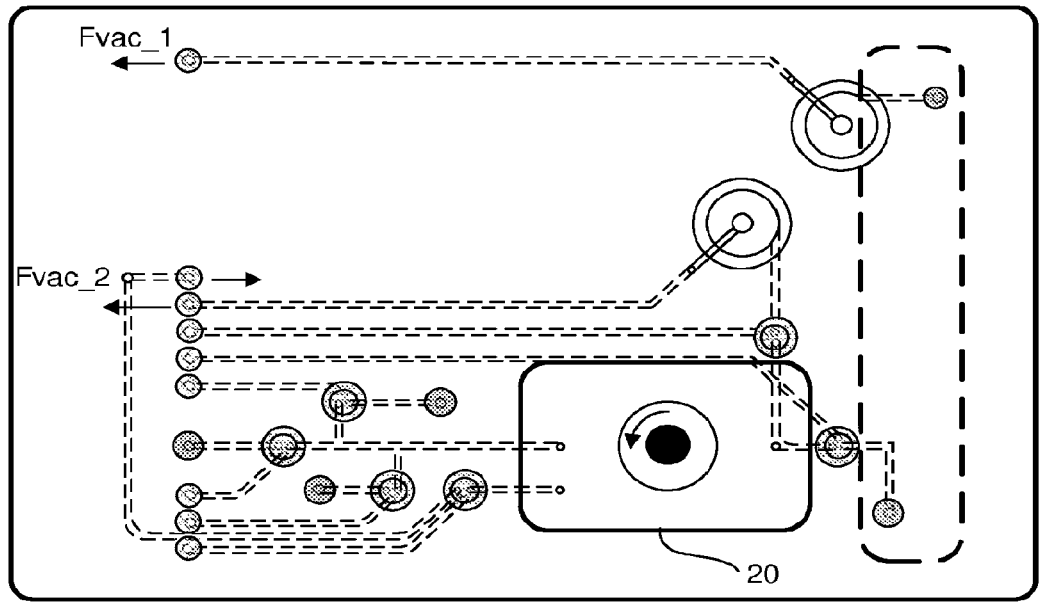
Figure 4K:
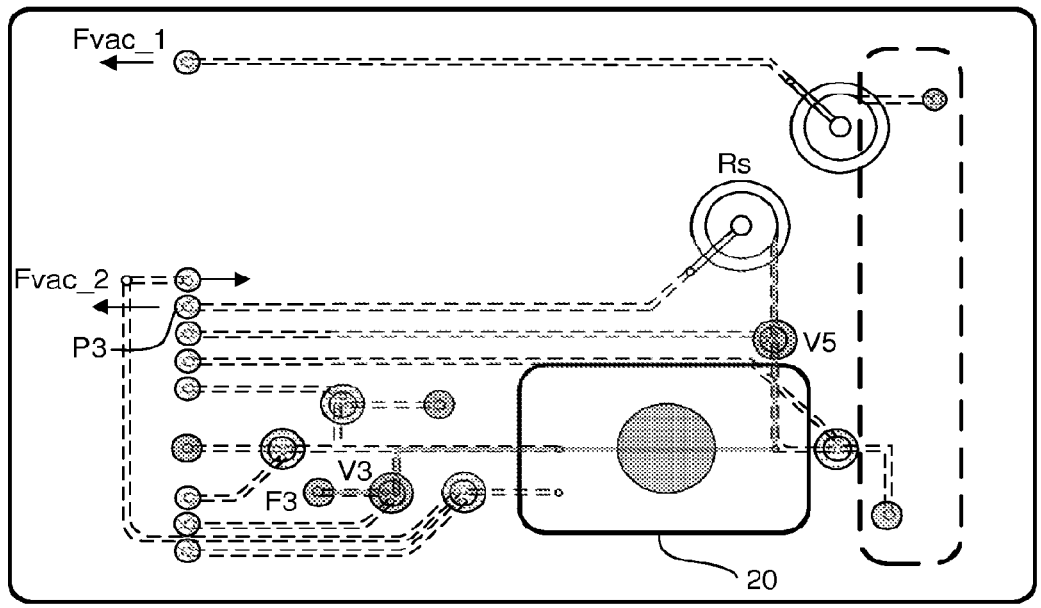
Figure 4L:
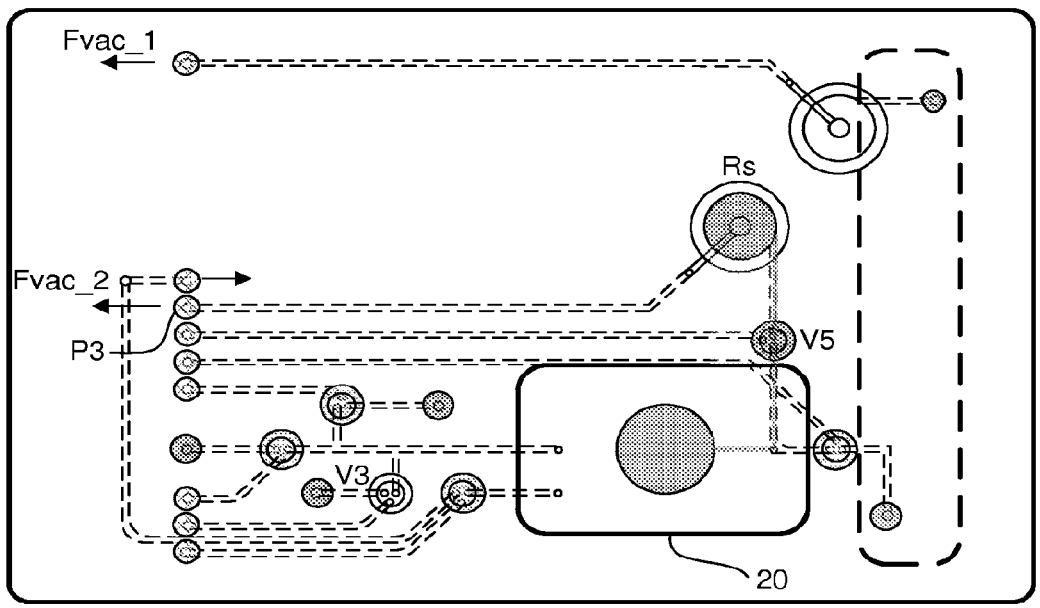
Figure 4M:
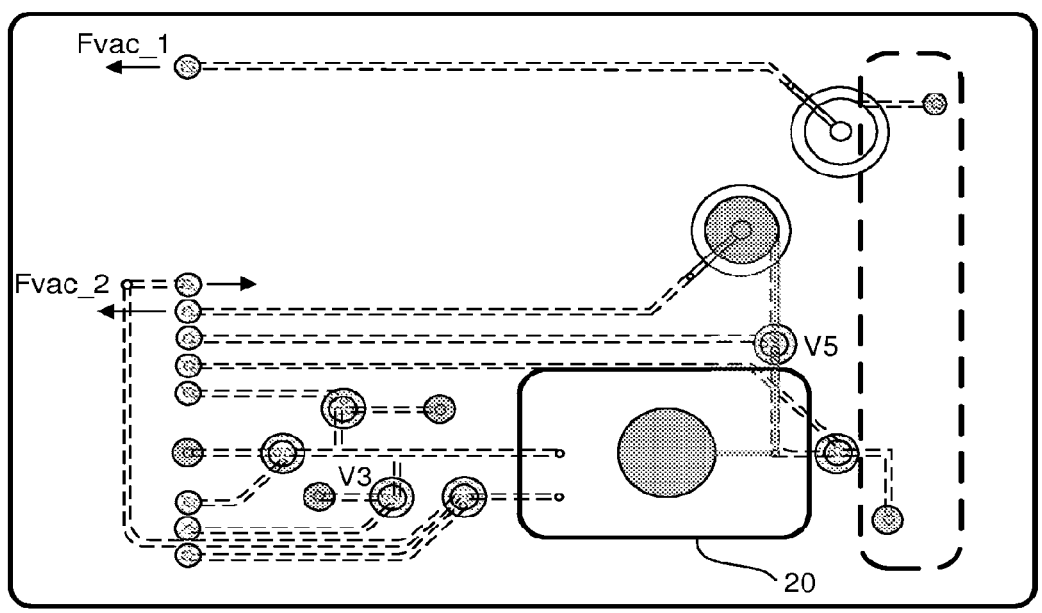
Figure 5A:
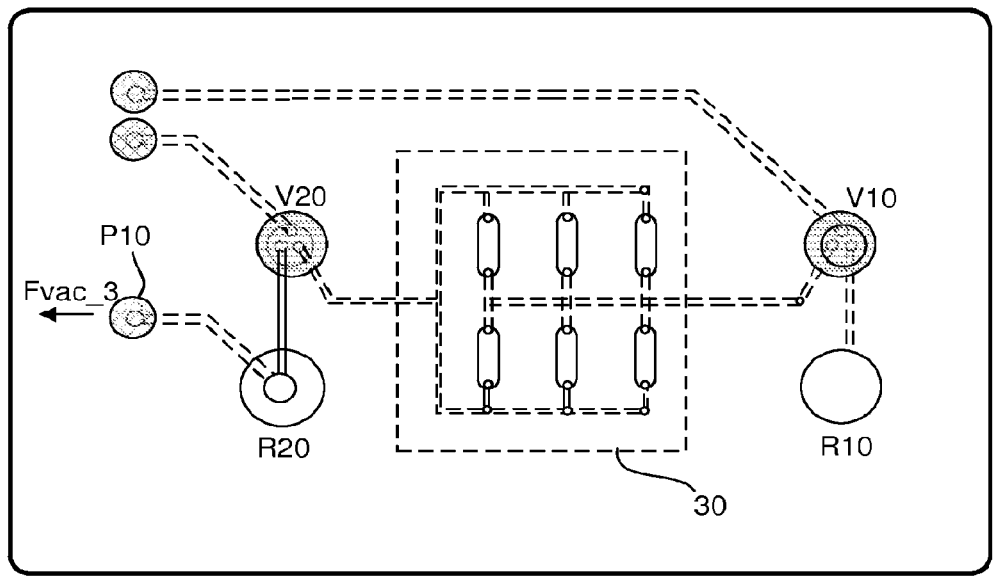
FIGS. 5A to 5G illustrate the various steps implemented in the fluid detection module used in the system of the invention.
Figure 5B:
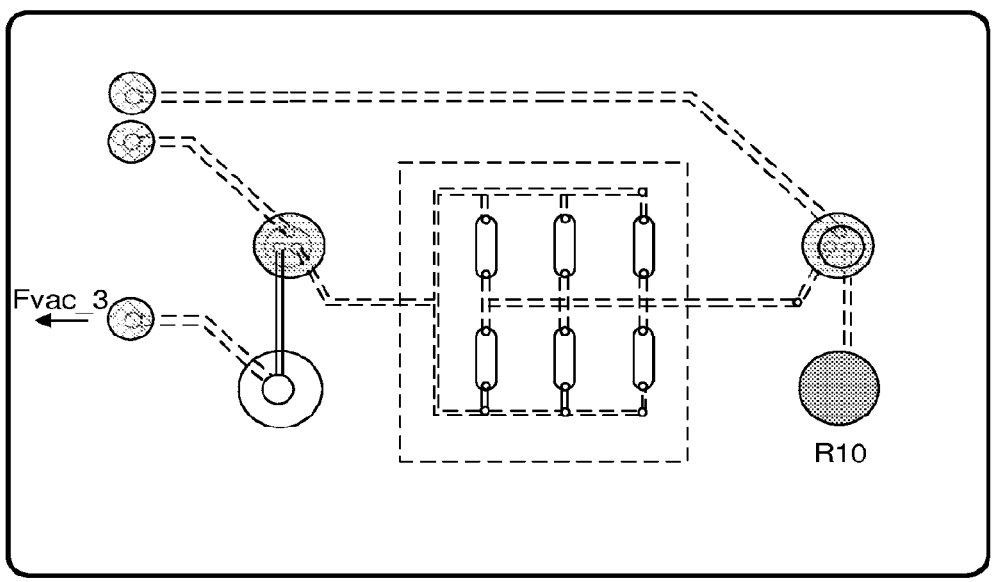
Figure 5C:
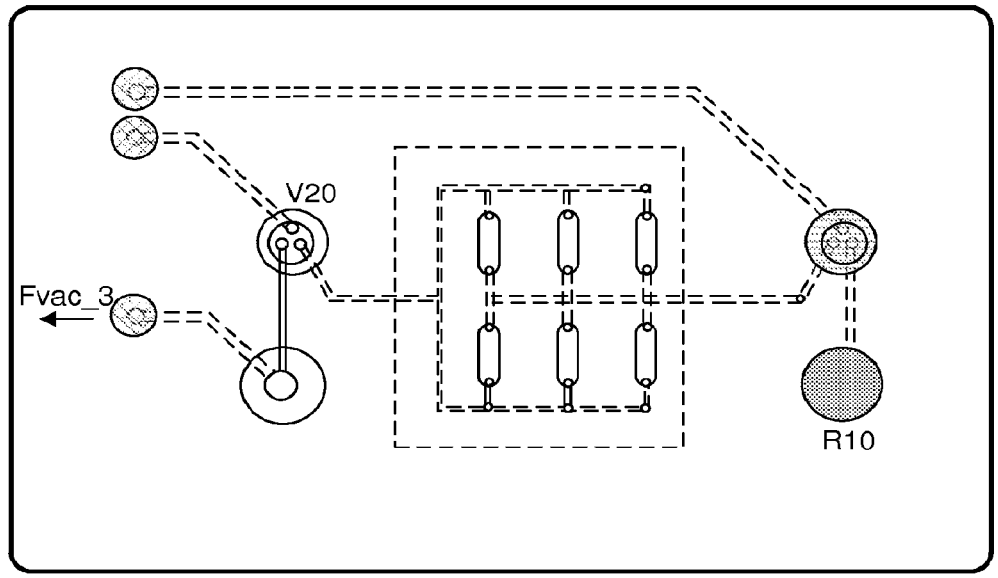
Figure 5D:
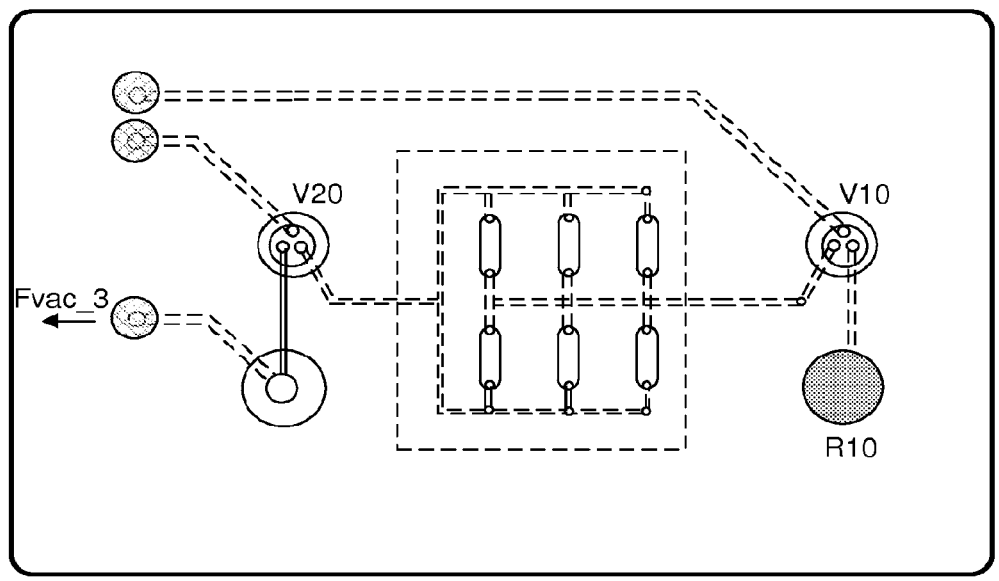
Figure 5E:
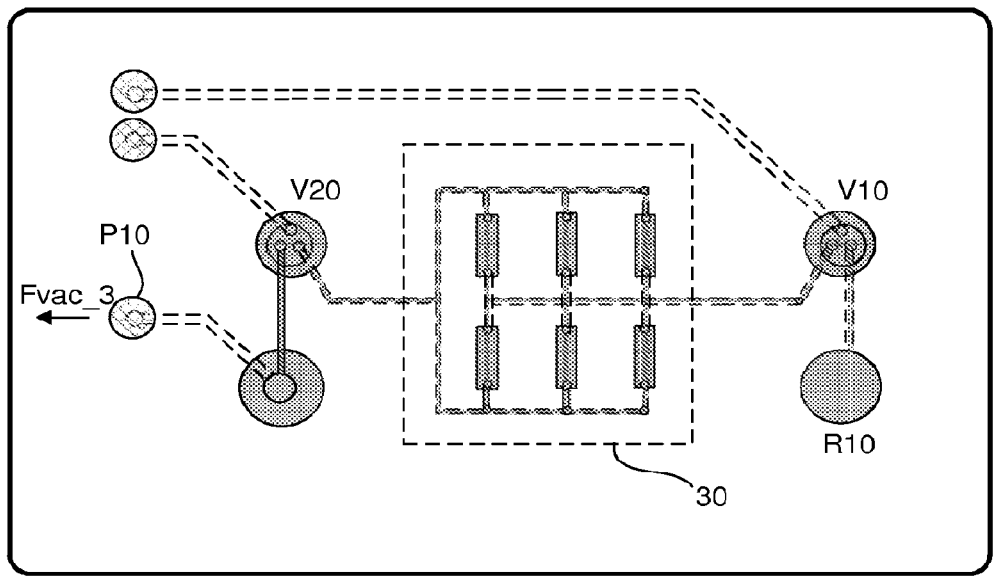
Figure 5F:
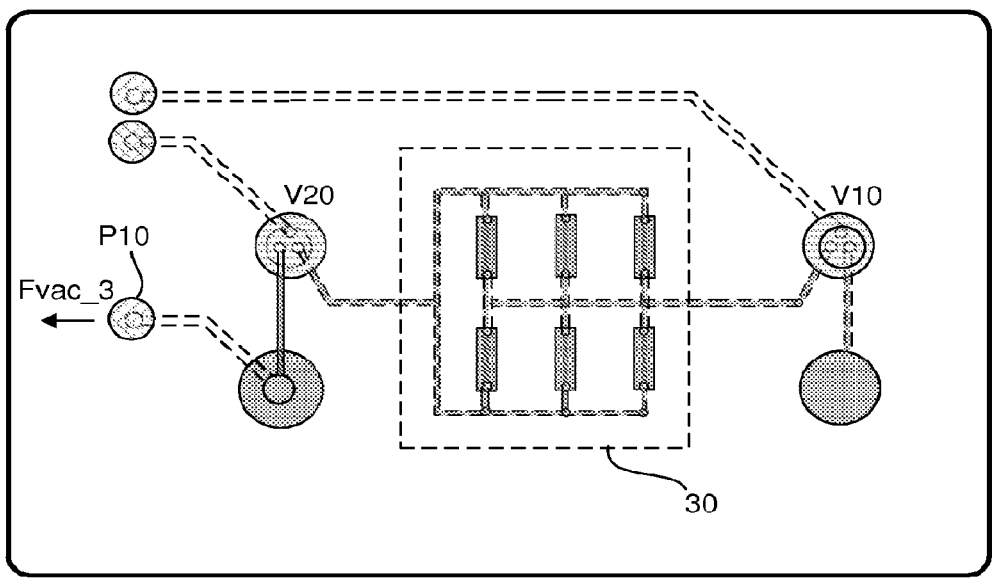
Figure 5G:
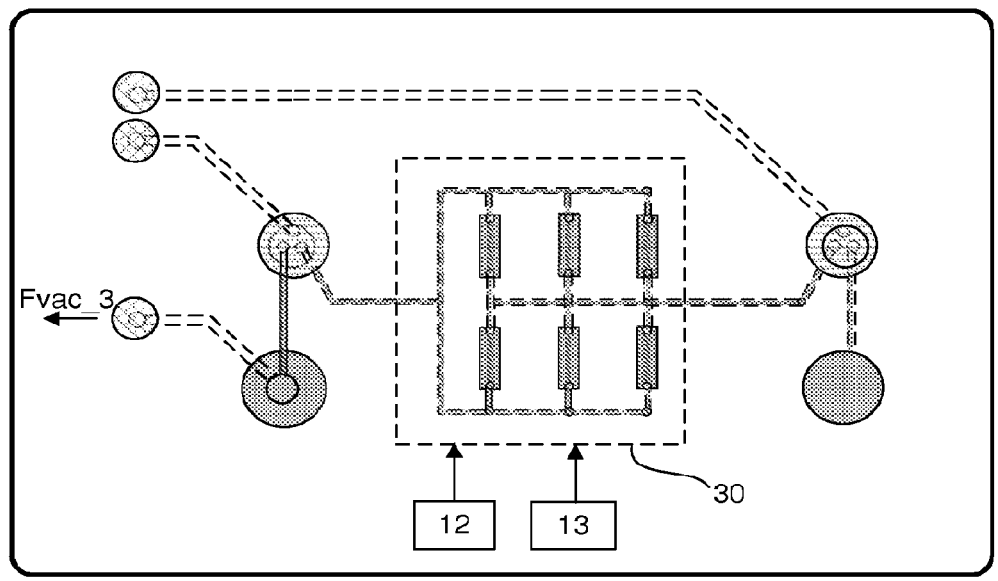

Generally and in a non-limiting manner, the first fluid module MF1 of the cartridge 2 may comprise in particular:
- a first injection location which is intended to receive the sample to be analyzed;
- a second injection location for injecting a rinsing liquid;
- a third injection location for injecting an elution liquid;
- a fluid concentration and lysis device 20 for the biological species present in the sample. In a non-limiting manner, this device 20 may have an architecture such as that illustrated in FIG. 3 and already described in the patent application EP3222989A1. It may thus comprise a concentration and lysis chamber 200 in which the sample is placed, a filter 201, an abrasive abutment surface 202 which is placed in the chamber 200 and against which the biological species can be ground and a flexible membrane 203 which can be deformed and which closes the chamber; another device architecture is also described in the patent application WO2015/181743A1;
- a storage reservoir for the sample obtained after concentration and lysis;
- a waste reservoir;
- a fluid circuit which is suitable for connecting the various elements of the module;
- a pneumatic circuit which comprises pneumatic inlets/outlets which are suitable for circulating the fluid between the elements through the fluid circuit.

Generally and in a non-limiting manner, the second fluid module MF2 of the cartridge 2 may comprise in particular:
- a first injection location of the sample to be analyzed, this first injection location being connected via a fluid connection to the storage reservoir of the first fluid module;
- a network of a plurality of different chambers which are supplied in parallel via a distribution channel which is connected to said first injection location of the analysis module;
- a fluid circuit which is suitable for joining the different elements of the module;
- a pneumatic circuit which comprises pneumatic inlets/outlets which are suitable for enabling fluid to circulate in the fluid circuit of the module.

The analysis device itself comprises the following elements:
- a plate 14 which forms a planar abutment surface for receiving said fluid cartridge 2 in a removable manner; after positioning on the plate, the cartridge 2 remains fixed;
- a mechanical assembly 10 composed of a spatula 100 or movable rod which is rotatably driven by a motor relative to the cartridge 2; the spatula 100 is controlled to move into abutment, via the outer side, against the flexible membrane 203 of the fluid concentration and lysis device 20 in order to draw out the membrane 203 toward the inner side of the chamber 200. The end of the spatula 100 is pressed on the membrane. By pressing on the membrane in order to draw it out toward the base of the chamber 200, the end of the spatula reaches the abrasive abutment surface 202 and crushes the biological species against said surface in order to release the DNA modules;

at least one heating unit 12 of the fluid chamber network, which is integrated in the plate 14 and located relative to the zone of the cartridge 2 carrying the chamber network. The heating unit 12 may comprise a Peltier element, a copper plate in order to homogenize the temperature, a thermal sensor which enables precise regulation of the temperature and where applicable a radiator and a fan in order to dissipate the heat;

a pneumatic system 11 which comprises one or more suction pumps in order to circulate the fluid sample in each fluid module MF1, MF2 of the cartridge and between the two modules. The pneumatic system 11 may also be used to generate a flow of air (suction force Fvac_1, Fvac_2, Fvac_3) through the filter 201 of the concentration and lysis device, in particular in order to dry it. The pneumatic system may also be configured to control each valve (of the pneumatic type) used in the two fluid modules MF1, MF2;

an optical fluorescence measurement system 13 which is arranged above the plate 14 and which may comprise a camera, LEDs and optical filters and which is configured to measure the fluorescence in each of the chambers of the network of the cartridge, during a DNA amplification reaction;

a man/machine interface MMI for controlling the analysis device 1;

a control and processing unit UC which may comprise at least one microprocessor and storage means. The control and processing unit UC is intended to carry out a command sequence. Depending on the type of analysis to be carried out and in accordance with the biological species to be targeted, the control and processing unit UC is configured to select the suitable control sequence. Units which are offset with respect to each hardware entity of the system will also be able to be used. The control and processing unit UC is also capable of processing the images captured by the optical measurement system 13. Based on these images, it is thus possible to increase to the DNA quantity of the sample present in each chamber of the network and therefore to the number of bacteria initially present in the sample initially taken in situ. The control and processing unit UC is also configured to store the results in a database DB which is stored locally or remotely and to carry out monitoring over time by comparing the data using different selection filters (sample location, type of sample, target, etc.).

According to a specific aspect of the invention illustrated in FIG. 2, the control and processing unit UC will be capable of carrying out several software modules M1, M2, M3 which are each intended to implement one of the steps E1, E2, E3 of the analysis process described above. Each of the software modules thereof will have the function of sending commands to the different entities of the device and/or processing the data received. With reference to FIG. 2, the following diagram thus applies:

the module M1 which is intended to implement the preparation step E1, including the concentration and lysis, is configured to send commands to the lysis and concentration device 10 and to the pneumatic system 11;

the module M2 which is intended to implement the detection step E2 is configured to send commands to the heating unit 12, to the pneumatic system 11 and to the optical measurement system 13;

the module M3 which is intended to implement the analysis step E3 is configured to receive images from the optical measurement system 13 and to process the images. Based on the images, it generates analysis results R. It may in particular use the database DB;

the man/machine interface MMI enables the analysis device to be configured and enables analysis parameters to be selected.

FIGS. 4A to 4M illustrate in detail the different steps implemented in the first fluid module MF1 which is intended for concentration and lysis. These Figures show the first fluid module MF1 which is produced on a card as described above. Advantageously, the module as illustrated thus comprises:

a plurality of pneumatic inlets/outlets Px which are intended to be connected to the pneumatic system of the analysis device when the cartridge is inserted into the device;

a plurality of fluid inlets Fy;

the concentration and lysis device 20;

a waste reservoir R1;

a plurality of two-way valves V1-V6 which can be controlled by the control and processing unit during execution of the sequence;

a storage reservoir Rs.

In this module MF1, the circulation of the various fluids is carried out by generating a suction force Fvac_1 or Fvac_2 generated by the pneumatic system of the device.

FIG. 4A

The module is in the initial state. The valves V1 to V6 are all closed.

FIG. 4B

This is the step of injecting the sample taken in the module. The sample can be injected at a volume of 1 ml.

The control and processing unit UC controls the opening of the valve V1 and the opening of the valve V6. The control and processing unit UC controls the pneumatic system 11 in order to generate via the inlet P1 a suction force Fvac_1 in order to draw the sample into the fluid circuit. The sample is introduced into the circuit via the fluid inlet F1 and then joins the chamber 200 of the concentration and lysis device 20 and passes through the filter 201 of the device 20. The portion of the sample which is not retained by the filter 201 is discharged toward the waste reservoir R1. The suction force Fvac_1 is maintained until the entire sample volume has passed through the filter.

FIG. 4C

Flowing through the filter 201, the sample is filtered by the filter 201. The surplus sample is discharged toward the waste reservoir R1.

FIG. 4D

The entire sample is filtered. The biological species present in the sample and retained by the filter are present in the chamber.

The control and processing unit UC controls the opening of the valve V4 and the pneumatic system 11. A suction force Fvac_1 is generated by the location P1 and creates a flow of air through the filter 201 in order to dry it. The air is drawn in via the location P2.

FIG. 4E

The control and processing unit controls the closure of the valves V1, V4 and V6. All the valves V1 to V6 are then closed.

FIG. 4F

The control and processing unit UC controls the opening of the valve V2 and the opening of the valve V6. The control and processing unit UC controls the pneumatic system 11 in order to generate via the location P1 the suction force Fvac_1 in order to draw the rinsing liquid via the fluid location F2 and to inject it into the chamber 200 in order to purify the filtered biological species. The rinsing liquid is discharged into the waste reservoir R1.

FIG. 4G

The rinsing is maintained. The rinsing liquid may be provided at a volume of 1 ml.

FIG. 4H

The control and processing unit controls the opening of the valve V4 and the pneumatic system 11. A suction force Fvac_1 is generated by the location P1 and creates a flow of air through the filter 201 in order to dry it. The air is drawn in via the location P2.

FIG. 4I

The control and processing unit controls the closure of the valves V2, V4 and V6. All the valves V1 to V6 are closed.

FIG. 4J

The control and processing unit UC controls the mechanical lysis assembly 10 in order to move the spatula 100 in a movement for grinding the biological species present in the chamber 200 against the abrasive abutment surface 202. The movement applied may be the combination of a rotation and translations. Following this lysis step, the chamber 200 contains pollutants and a biological material (DNA molecules) to be analyzed.

FIG. 4K

The control and processing unit UC controls the opening of the valve V3 and the opening of the valve V5.

The control and processing unit UC controls the pneumatic system in order to generate the suction force Fvac_2 via the location P3 in order to draw in an elution liquid via the fluid location F3 toward the chamber 200 and through the filter 201 in order to elute the biological material obtained after the lysis.

The elution liquid containing the targeted biological material is collected in a storage reservoir Rs. This elution liquid may be injected at a volume of 50 µl.

FIG. 4L

The elution liquid containing the targeted biological material is collected in the storage reservoir Rs.

FIG. 4M

The control and processing unit controls the closure of the valves V3 and V5. The concentration and lysis process is then terminated.

In this first fluid module MF1, it should be noted that hydrophobic filters are placed in the circuit so that no liquid is introduced into the device. These filters are integrated in the cartridge, between the pneumatic inlets/outlets and the remainder of the fluid circuit. Furthermore, they also allow the filling of the volumes by means of suction to be better adjusted. This is because these filters allow the gases required for the suction of the liquid into the fluid module to pass but do not allow the liquids to pass.

After the relevant biological material has been collected in the storage reservoir Rs, it may be transferred or injected into the second fluid module MF2 of the cartridge for detection.

FIGS. 5A to 5G illustrate in detail the different steps implemented in this second fluid module MF2 which is intended for the detection of the biological material recovered from the initial sample. These Figures show the second fluid module MF2 produced on a card as described above. Advantageously, it should be noted that the two modules MF1, MF2 can be produced on the same card. Advantageously, the module MF2 as illustrated thus comprises:

- a plurality of pneumatic inlets/outlets Px which are intended to be connected to the pneumatic system 11 of the analysis device 1 when the cartridge 2 is inserted into the device;
- an inlet reservoir R10 in which the sample to be analyzed is placed, this reservoir being able to be identical to the process end storage reservoir Rs used in the first module;
- an outlet reservoir R20;
- a network 30 of six detection chambers which are supplied in parallel by a central distribution channel;
- a plurality of three-way valves V10, V20 which can be controlled by the control and processing unit US when the analysis sequence is carried out.

In this module, the circulation of the various fluids is carried out by generating a suction force Fvac_3 generated by the pneumatic system 11 of the device via the inlet P10.

FIG. 5A

The module is in the initial state. The valves V10 and V20 are both closed.

FIG. 5B

The sample containing the biological material to be analyzed is placed in the inlet reservoir R10. This reservoir may be common to the storage reservoir Rs of the first fluid module MF1.

FIG. 5C

The control and processing unit UC controls the opening of the valve V20.

FIG. 5D

The control and processing unit controls the opening of the valve V10.

FIG. 5E

The control and processing unit UC controls the pneumatic system 11 in order to generate a suction force Fvac_3 via the location P10 in order to draw the sample in the fluid circuit out of the reservoir R10. The sample is introduced into the central distribution channel and, simultaneously, into the six parallel chambers of the network 30. The architecture of the network 30 of chambers enables it to be ensured that the chambers are all filled at the same time.

FIG. 5F

The control and processing unit UC controls the closure of the valve V10 and the closure of the valve V20 after all the chambers of the network are filled.

Each chamber may comprise a different amplification reagent in order to detect the presence of different biological species.

FIG. 5G

The control and processing unit UC can then control the heating unit 12 of the device in order to subject the biological material present in each chamber of the network 30 to one or more thermal cycles.

The control and processing unit UC also controls the optical measurement system 13 in order to capture fluorescence images in each chamber of the network 30.

After the images have been captured, they are recorded, then analyzed by the control and processing unit UC in order to determine which biological species are present and the quantities in which they are present. The control and processing unit UC may also refer to the analyses carried out beforehand in order to highlight upward or downward trends. Results R are then generated by the control and processing unit UC.

Advantageously, the fluid modules MF1, MF2 may use hydrophobic filters in order to enable filling operations in suction mode with a precise volume.

In the second fluid module MF2, a dead volume may be integrated in the central distribution channel in order to trap the air bubbles generated when filling the chambers of the network 30. In the same manner, each chamber of the network 30 may have a limited height in order to prevent the formation of bubbles at the inlet.

Advantageously, each valve of the fluid modules can use a seal made of EPDM in order to improve the sealing of the circuits and to prevent the injection of air into the circuits when the valve is closed.

Figure 6:
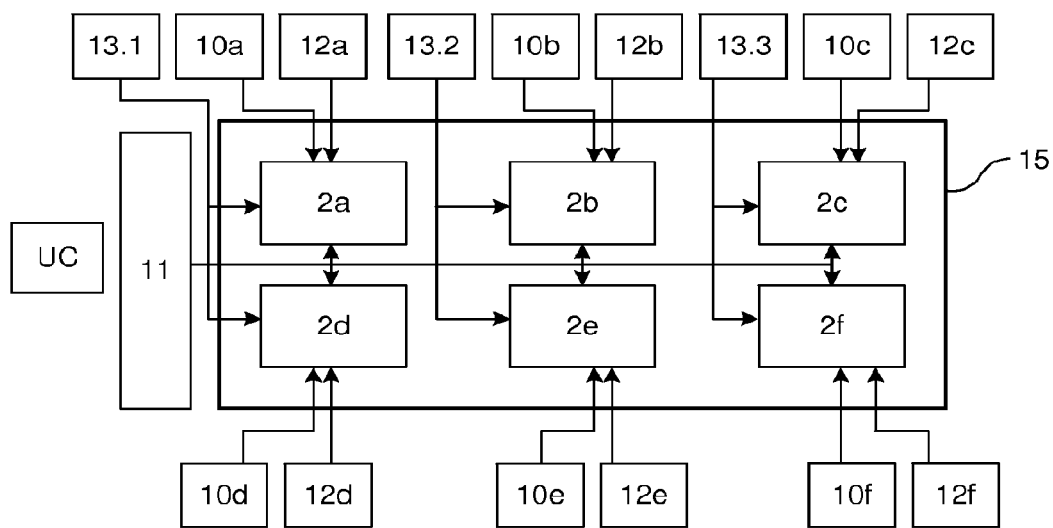
FIG. 6 shows an advantageous construction variant of the preparation, detection and analysis system of the invention.

According to a specific aspect of the invention illustrated in FIG. 6, the device may be adapted to process a plurality of cartridges simultaneously, for example, six cartridges 2a, 2b, 2c, 2d, 2e, 2f. These will be loaded onto a cassette 15 which is positioned on the plate 14 of the device which thus contains a pneumatic system 11 common to all the cartridges with a number of adapted inlets/outlets, six mechanical assemblies 10a, 10b, 10c, 10d, 10e, 10f which can be activated in order to carry out the lysis in each cartridge, six heating zones 12a, 12b, 12c, 12d, 12e, 12f and three cameras 13.1, 13.2, 13.3 which each move between two positions in order to image the six cartridges. The control and processing unit UC naturally enables the different entities to be controlled and the images which are captured to be collected in order to process them.

In this manner, the preparation, detection and analysis system of the invention has the following advantages:
- it can be readily transported in an industrial environment;
- it enables a rapid analysis of a sample (no more than a few hours);
- it is simple to use since it enables a transition from the sample to the result in an automated manner, limiting the intervention of an operator to the greatest possible extent;
- it is compatible with complex samples, for example, with a high salt content containing, for example, dissolved solids, free or dissolved hydrocarbons, high concentrations of cations, acidic pH levels originating from industrial installations;
- it can be adapted to the targets to be detected, for a specific taxonomic group or for a relevant metabolic function (for example, sulfate-reducing bacteria) and as a result of its structure enables the simultaneous analysis of several species/functions or groups of species/functions;
- it enables qualitative and quantitative results to be obtained (as a result of the Q-PCR with calibration);
- it is sensitive, the detection limit thereof being less than $10^3$ cfu/mL;
- it enables, using a database, the qualitative and quantitative development data of the biological species detected over time to be made available.

The invention claimed is:

1. An automated preparation, detection and analysis system for a first fluid sample containing biological species, said preparation, detection and analysis system comprising:
   at least one fluid cartridge which comprises at least one fluid concentration and lysis module and a fluid detection module including a network of a plurality of amplification chambers which are arranged in parallel relative to a fluid distribution channel, said fluid lysis and concentration module including a concentration and lysis device which includes a preparation chamber, an abrasive abutment surface which is produced in said preparation chamber, a filter and a flexible and deformable membrane which closes said chamber, and
   a device comprising:
      a frame which is provided with at least one plate which is intended to receive said fluid cartridge in a removable manner,
      a mechanical assembly comprising at least one movable rod which is fixed to said frame and which comprises a free end which is arranged to cooperate with said flexible membrane of the fluid lysis and concentration module,
      a pneumatic system controlled to enable circulation of a fluid through said cartridge,
      at least one heating unit which is carried by the plate and which is arranged in order to heat the network of chambers in parallel during a cyclical or isothermal amplification reaction,
      an optical system for measuring fluorescence through one or more of the amplification chambers of the fluid detection module of the cartridge,
      a control and processing unit which is configured to implement an analysis sequence by being configured to
         control the pneumatic system in order to inject the first fluid sample through the filter of the concentration and lysis device in order to recover the biological species present in the first sample,
         control the pneumatic system in order to generate a flow of drying air in a fluid circuit of the fluid concentration and lysis module, said fluid circuit passing through said filter of the concentration and lysis device,
         control the mechanical assembly in order to activate the rod in an abutment movement of the flexible membrane against the abrasive abutment surface in order to lyse the biological species contained in the first fluid sample,
         control the pneumatic system in order to discharge a second fluid sample out of the preparation chamber to said fluid distribution channel of the cartridge,
         control the pneumatic system in order to fill in parallel and in a simultaneous manner the amplification chambers of the network with the second fluid sample,
         control the heating unit in order to heat said second fluid sample present in each chamber of the network,
         control the optical measurement system in order to measure the fluorescence in each amplification chamber containing a fraction of the second fluid sample,
         record the fluorescence measurement results, and
         apply an analysis algorithm to the measurement results obtained and generating qualitative and quantitative data of the biological species present in the first fluid sample.

2. The system as claimed in claim 1, wherein the control and processing unit is configured to carry out:
   a first module which is configured to send commands to the concentration and lysis device and to the pneumatic system,
   a second module which is configured to send commands to the heating unit, to the pneumatic system and to the optical measurement system, a third module which is configured to receive images from the optical measurement system and to process the images.

3. The system as claimed in claim 2, further comprising a database which stores the previous analysis results, wherein the third module is configured to refer to said database in order to generate concentration variation curves for each biological species detected.

4. The system as claimed in claim 1, wherein each fluid module may comprise hydrophobic filters which are arranged on pneumatic channels which are connected directly to the pneumatic system.

5. The system as claimed in claim 1, wherein the fluid concentration and lysis module and the fluid detection module comprises a plurality of fluid valves which can be controlled by the control and processing unit.

6. The system as claimed in claim 1, further comprising a cartridge which integrates n fluid cartridges, with n being greater than or equal to 2.

7. The system as claimed in claim 6, further comprising:
   n mechanical assemblies which each comprise at least one rod which is associated with each cartridge,
   n heating units which are each arranged in order to heat the network of chambers of each cartridge, and
   n/2 optical fluorescence measurement system which is configured to move between two positions in order to image the n cartridges of the system.

8. A preparation, detection and analysis method for a fluid sample, implemented using a system for a first fluid sample containing biological species, said system including at least one fluid cartridge which comprises at least one fluid concentration and lysis module and a fluid detection module including a network of a plurality of amplification chambers which are arranged in parallel relative to a fluid distribution channel, said fluid lysis and concentration module including a concentration and lysis device which includes a preparation chamber, an abrasive abutment surface which is produced in said preparation chamber, a filter and a flexible and deformable membrane which closes said chamber, and a device including: a frame which is provided with at least one plate which is intended to receive said fluid cartridge in a removable manner, a mechanical assembly comprising at least one movable rod which is fixed to said frame and which comprises a free end which is arranged to cooperate with said flexible membrane of the fluid lysis and concentration module, a pneumatic system controlled to enable circulation of a fluid through said cartridge, at least one heating unit which is carried by the plate and which is arranged in order to heat the network of chambers in parallel during a cyclical or isothermal amplification reaction, an optical system for measuring fluorescence through one or more of the amplification chambers of the fluid detection module of the cartridge, a control and processing unit which is configured to implement an analysis sequence by being configured to control the pneumatic system in order to inject the first fluid sample through the filter of the concentration and lysis device in order to recover the biological species present in the first sample, control the pneumatic system in order to generate a flow of drying air in a fluid circuit of the fluid concentration and lysis module, said fluid circuit passing through said filter of the concentration and lysis device, control the mechanical assembly in order to activate the rod in an abutment movement of the flexible membrane against the abrasive abutment surface in order to lyse the biological species contained in the first fluid sample, control the pneumatic system in order to discharge a second fluid sample out of the preparation chamber to said fluid distribution channel of the cartridge, control the pneumatic system in order to fill in parallel and in a simultaneous manner the amplification chambers of the network with the second fluid sample, control the heating unit in order to heat said second fluid sample present in each chamber of the network, control the optical measurement system in order to measure the fluorescence in each amplification chamber containing a fraction of the second fluid sample, record the fluorescence measurement results, and apply an analysis algorithm to the measurement results obtained and generating qualitative and quantitative data of the biological species present in the first fluid sample, the method comprising:
   controlling the pneumatic system in order to inject the first fluid sample through the filter of the concentration and lysis device in order to recover the biological species present in the first sample,
   controlling the pneumatic system in order to generate a flow of drying air in a fluid circuit of the fluid concentration and lysis module, said fluid circuit passing through said filter of the concentration and lysis device,
   controlling the mechanical assembly in order to activate the rod in a movement for abutting the flexible membrane against the abrasive abutment surface in order to lyse the biological species contained in the first fluid sample,
   controlling the pneumatic system in order to discharge a second fluid sample out of the preparation chamber to said fluid distribution channel of the cartridge,
   controlling the pneumatic system in order to fill in parallel and in a simultaneous manner the amplification chambers of the network with the second fluid sample,
   controlling the heating unit in order to heat said second fluid sample present in each chamber of the network,
   controlling the optical measurement system in order to measure the fluorescence in each amplification chamber containing a fraction of the second fluid sample,
   recording the fluorescence measurement results,
   applying an analysis algorithm to the measurement results obtained, and generating qualitative and quantitative data of the biological species present in the first fluid sample.

9. A non-transitory computer readable medium having stored thereon a program that when executed by a computer causes the computer to implement a preparation, detection and analysis method for a fluid sample using a system for a first fluid sample containing biological species, said system including at least one fluid cartridge which comprises at least one fluid concentration and lysis module and a fluid detection module including a network of a plurality of amplification chambers which are arranged in parallel relative to a fluid distribution channel, said fluid lysis and concentration module including a concentration and lysis device which includes a preparation chamber, an abrasive abutment surface which is produced in said preparation chamber, a filter and a flexible and deformable membrane which closes said chamber, and a device including: a frame which is provided with at least one plate which is intended to receive said fluid cartridge in a removable manner, a mechanical assembly comprising at least one movable rod which is fixed to said frame and which comprises a free end which is arranged to cooperate with said flexible membrane of the fluid lysis and concentration module, a pneumatic system controlled to enable circulation of a fluid through said cartridge, at least one heating unit which is carried by the plate and which is arranged in order to heat the network of chambers in parallel during a cyclical or isothermal amplification reaction, an optical system for measuring fluorescence through one or more of the amplification chambers of the fluid detection module of the cartridge, a control and processing unit which is configured to implement an analysis sequence by being configured to control the pneumatic system in order to inject the first fluid sample through the filter of the concentration and lysis device in order to recover the biological species present in the first sample, control the pneumatic system in order to generate a flow of drying air in a fluid circuit of the fluid concentration and lysis module, said fluid circuit passing through said filter of the concentration and lysis device, control the mechanical assembly in order to activate the rod in an abutment movement of the flexible membrane against the abrasive abutment surface in order to lyse the biological species contained in the first fluid sample, control the pneumatic system in order to discharge a second fluid sample out of the preparation chamber to said fluid distribution channel of the cartridge, control the pneumatic system in order to fill in parallel and in a simultaneous manner the amplification chambers of the network with the second fluid sample, control the heating unit in order to heat said second fluid sample present in each chamber of the network, control the optical measurement system in order to measure the fluorescence in each amplification chamber containing a fraction of the second fluid sample, record the fluorescence measurement results, and apply an analysis algorithm to the measurement results obtained and generating qualitative and quantitative data of the biological species present in the first fluid sample, the method comprising:

controlling the pneumatic system in order to inject the first fluid sample through the filter of the concentration and lysis device in order to recover the biological species present in the first sample, controlling the pneumatic system in order to generate a flow of drying air in a fluid circuit of the fluid concentration and lysis module, said fluid circuit passing through said filter of the concentration and lysis device, controlling the mechanical assembly in order to activate the rod in a movement for abutting the flexible membrane against the abrasive abutment surface in order to lyse the biological species contained in the first fluid sample, controlling the pneumatic system in order to discharge a second fluid sample out of the preparation chamber to said fluid distribution channel of the cartridge, controlling the pneumatic system in order to fill in parallel and in a simultaneous manner the amplification chambers of the network with the second fluid sample, controlling the heating unit in order to heat said second fluid sample present in each chamber of the network, controlling the optical measurement system in order to measure the fluorescence in each amplification chamber containing a fraction of the second fluid sample, recording the fluorescence measurement results, applying an analysis algorithm to the measurement results obtained, and generating qualitative and quantitative data of the biological species present in the first fluid sample.

\* \* \* \* \*